(12) United States Patent  (10) Patent No.: US 8,322,341 B2
Koeller  (45) Date of Patent: Dec. 4, 2012

(54) SYSTEM AND METHOD FOR OCCLUDING A REPRODUCTIVE BODY LUMEN

(75) Inventor: Gregory L. Koeller, Apple Valley, MN (US)

(73) Assignee: Conceptus, Inc., Mountain View, CA (US)

( * ) Notice: Subject to any disclaimer, the term of this patent is extended or adjusted under 35 U.S.C. 154(b) by 478 days.

(21) Appl. No.: 12/556,262

(22) Filed: Sep. 9, 2009

(65) Prior Publication Data

US 2010/0059062 A1   Mar. 11, 2010

Related U.S. Application Data

(60) Provisional application No. 61/095,340, filed on Sep. 9, 2008.

(51) Int. Cl.
*A61F 6/06* (2006.01)
*A61B 19/00* (2006.01)

(52) U.S. Cl. .......................... 128/831; 128/830; 128/898

(58) Field of Classification Search .......... 128/831–833, 128/838, 839–843, 847, 887; 623/1.11, 1.18, 623/1.2; 606/135–137, 153, 193
See application file for complete search history.

(56) References Cited

U.S. PATENT DOCUMENTS

| | | | |
|---|---|---|---|
| 5,935,098 A * | 8/1999 | Blaisdell et al. | 604/515 |
| 5,935,137 A * | 8/1999 | Saadat et al. | 606/135 |
| 6,096,052 A | 8/2000 | Callister et al. | |
| 6,432,116 B1 | 8/2002 | Callister et al. | |
| 6,763,833 B1 * | 7/2004 | Khera et al. | 128/830 |
| 7,073,504 B2 | 7/2006 | Callister et al. | |
| 7,591,268 B2 * | 9/2009 | Lowe et al. | 128/830 |
| 8,181,653 B2 * | 5/2012 | Tal et al. | 128/831 |
| 2001/0041900 A1 | 11/2001 | Callister et al. | |
| 2005/0045183 A1 | 3/2005 | Callister et al. | |
| 2005/0085844 A1 | 4/2005 | Tremulis et al. | |
| 2005/0192616 A1 | 9/2005 | Callister et al. | |
| 2005/0209633 A1 | 9/2005 | Callister et al. | |
| 2006/0009798 A1 | 1/2006 | Callister et al. | |
| 2007/0261699 A1 | 11/2007 | Callister et al. | |
| 2008/0135053 A1 * | 6/2008 | Gruber et al. | 128/831 |
| 2008/0135054 A1 | 6/2008 | Callister et al. | |
| 2008/0308110 A1 | 12/2008 | Callister et al. | |
| 2009/0178682 A1 * | 7/2009 | Tal et al. | 128/831 |

FOREIGN PATENT DOCUMENTS

| | | |
|---|---|---|
| WO | WO/2007/133222 | 11/2007 |
| WO | WO/2009/017680 | 2/2009 |
| WO | WO/2009/075800 | 6/2009 |

* cited by examiner

*Primary Examiner* — Nicholas Lucchesi
*Assistant Examiner* — Kari Petrik
(74) *Attorney, Agent, or Firm* — Blakely, Sokoloff, Taylor & Zafman LLP

(57) ABSTRACT

An occluding system is provided that can include a first occluding device (e.g., secondary occluder) and a second occluding device (e.g., primary occluder). Providing two devices can better promote effective occlusion within the body lumen and facilitate advantageous occlusion stages, such as initial and long-term occlusion stages. In various embodiments, the two occluding devices are in operative communication with one another, such that the second occluding device is adapted to couple with or slide along a tail portion of the first occluding device.

8 Claims, 5 Drawing Sheets

SYSTEM AND METHOD FOR OCCLUDING A REPRODUCTIVE BODY LUMEN

RELATED APPLICATION

This application claims priority to and the benefit of U.S. Provisional Application No. 61/095,340, filed Sep. 9, 2008, which is incorporated herein by reference in its entirety.

FIELD OF THE INVENTION

The present invention relates generally to the field of occluding devices, delivery systems for such devices and the method of using such devices and systems in the occlusion of body lumens or passageways. The invention is particularly useful for the occluding reproductive lumens such as a female patient's fallopian tubes or a male patient's vas deferens to affect contraception.

BACKGROUND OF THE INVENTION

One form of contraception involves the occlusion of reproductive tracts, particularly, the fallopian tubes in female subjects and the vas deferens in male subjects, with an embolic material and/or occluding device that acutely and/or chronically (following foreign body tissue reaction or epithelialization) blocks passage of sperm through the reproductive tract. Particular forms of occluding devices and systems and methods of inserting the occluding devices in the vas deferens or fallopian tubes are described in commonly owned U.S. Pat. Nos. 6,096,052 and 6,432,116 and in commonly assigned U.S Patent Application Publication Nos. 2001/0041900, 2005/0045183, 2005/0085844, 2005/0192616, 2005/0209633, and 2006/0009798, for example, certain features of which are embodied in the Ovion® permanent contraceptive system sold by the assignee of the present invention.

It would be desirable to provide contraceptive occlusion systems that provide improved delivery and deployment systems, implant structures, and the effectiveness of occlusion.

SUMMARY OF THE INVENTION

The present invention is directed to a contraceptive or occluding system for occluding a reproductive tract or lumen to prevent the passage of reproductive cells there through. The occluding system can include a first occluding device (e.g., secondary occluder) and a second occluding device (e.g., primary occluder). Providing two devices can better promote effective occlusion within the body lumen and facilitate advantageous occlusion stages, such as initial and long-term occlusion stages. In various embodiments, the two occluding devices are in operative communication with one another to facilitate insertion, deployment and effective occlusion within the body lumen to prevent the passage of reproductive cells, eggs or sperm cells.

A relatively quick initial primary occlusion occurs when the second occluding device is inserted into the ostium and a secondary long-term occlusion occurs with the insertion of the first occluding device within the fallopian tubes (e.g., via obstruction and tissue in-growth within the device). As such, the second device serves as a primary occluder and the first device serves as a secondary occluder. A third mechanism for occlusion and contraception is provided for those embodiments where a tail of the first occluding device is left to extend into the uterus as an intrauterine device.

In various embodiments, the second occluding device can include a lumen there through adapted to receive and travel along a length of the tail of the first occluding device. Further, the second occluding device can include protruding members or textured portions to grab onto the tail, and the outer surface of the second occluding device can include protruding members or textured portions to facilitate fixation within or against the ostium tissue.

A catheter delivery system can be used to insert and position the first occluding device within the fallopian tubes of the patient. A needle delivery tool can be utilized to insert and position the second occluding device within the ostium of the patient. In other embodiments, a single delivery system can be employed to insert and deploy both the first and second occluding devices.

Various embodiments of the occluding device or member will include structures and materials to promote occlusion, such as denuding features, gels, frames, coatings, and the like.

Various contraceptive occlusion devices and delivery systems disclosed in U.S. Patent Application Publication Nos., 2005/0045183, 2005/0209633, 2006/0009798 and 2008/0308110, as well as PCT Patent Application Publication No. 2007/133222 can be employed, in whole or in part, with the present invention. As a result, each of the above-identified disclosures and publications is incorporated herein by reference in its entirety.

DETAILED DESCRIPTION OF PREFERRED EMBODIMENTS

Figure 1:
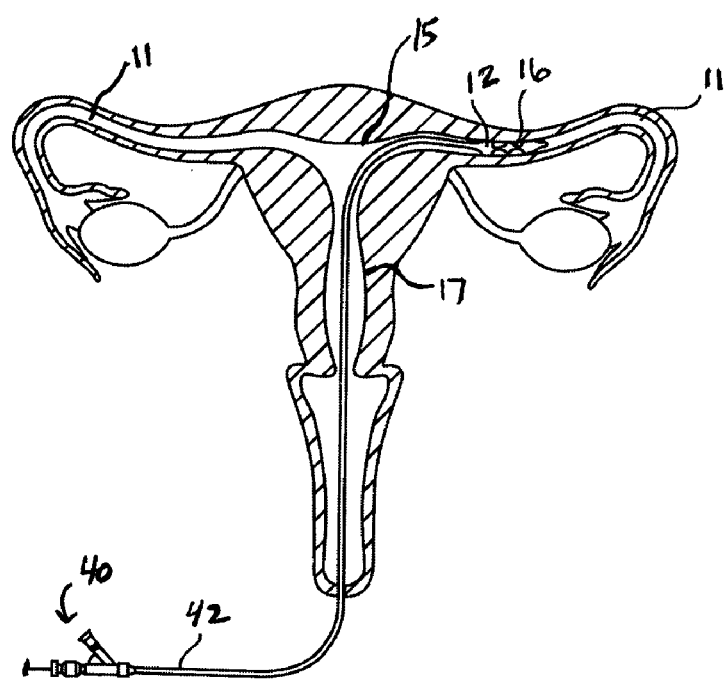
FIG. 1 schematically shows the delivery and insertion of an occluding device within a female's fallopian tube in accordance with embodiments of the present invention.

In the following detailed description, references are made to illustrative embodiments of methods and apparatus for carrying out the invention. It is understood that other embodiments can be utilized without departing from the scope of the invention. Preferred methods and apparatus are described for occlusion of reproductive body lumens to affect contraception.

It will be understood that the term "contraceptive device," "occlude," "occluding device," "implant," "occluding implant" or "occluding member" encompass any type of a device adapted to be delivered into and released or otherwise disposed in a reproductive tract or lumen to acutely and/or chronically occlude the reproductive tract lumen.

Referring generally to FIGS. 1-16, a contraceptive occluding system 10 is provided. The occluding system 10 can include a first occluding implant or device 12 (e.g., secondary occluder) and a second occluding implant or device 14 (e.g., primary occluder). Providing two devices can better promote effective occlusion within the body lumen and facilitate advantageous occlusion stages, such as initial and long-term occlusion stages. In various embodiments, the occluding devices 12, 14 are in operative communication with one another to facilitate insertion, deployment and effective occlusion within the body lumen to prevent the passage of reproductive cells, eggs or sperm cells.

In one embodiment, as shown in FIGS. 3-9, the first occluding device 12 can include a tubular member 16 having a first end 18, a second end 21, and a lumen extending there between. The tubular member 16 can be constructed and configured to support or promote tissue in-growth.

The tubular member 16 of the first occluding device 12 may be constructed of compatible mesh, Nitinol, length of shape-memory hypodermic tubing, shape-memory wire, slotted plastic or metal tubing, braided tubing or material, and can take on or resemble the shape of a ribbon, ring, coil, spring, and a myriad of other shapes and designs. Various exemplary configurations of the tubular member 16 are depicted in FIGS. 3-9. Further, the tubular member 16 can include bundled strands, woven strands, polymers, metals, protrusions or extending portions, treated animal tissues and like structures or designs to promote epithelialization and tissue in-growth. For instance, polyester or other polymer fibers may be attached to one or more expandable segments of the tubular member 16 to bear against the fallopian tube 11 wall such that tissue fixation and in-growth into the lumen occurs more rapidly. Additionally, the tubular member 16 may be surface coated or impregnated with epithelialization-promoting agents, drugs or other materials to enhance tissue impregnation.

A slow-release contraceptive substance may also be embedded with one or more of the devices 12, 14 to facilitate contraception during the time that it takes for tissue in-growth to occur, as disclosed in the above-referenced U.S. Patent Application Publication Nos. 2005/0045183 and 2006/000798, for example. The occluding devices 12, 14 may take other forms as shown in the various embodiments of occluding devices depicted in the incorporated patent references, or as otherwise known in the art.

Figure 2:
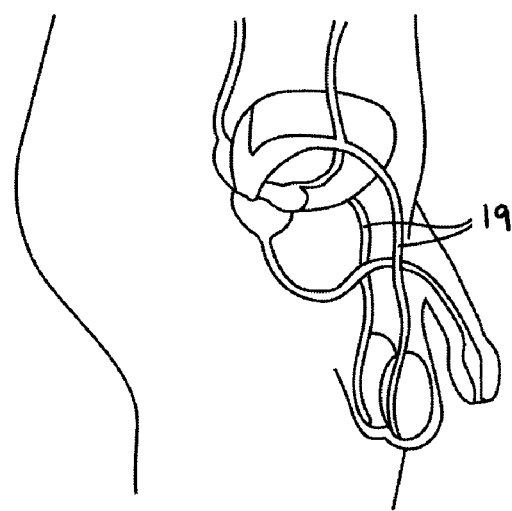
FIG. 2 schematically shows the relevant male anatomy, including the vas deferens.
Figure 3:
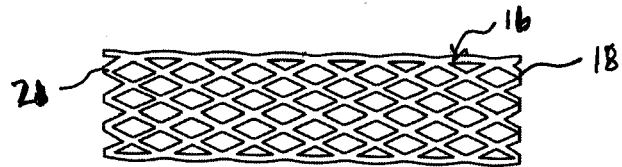
FIGS. 3-9 show exemplary tubular members of an occluding device in accordance with embodiments of the present invention.
Figure 4:
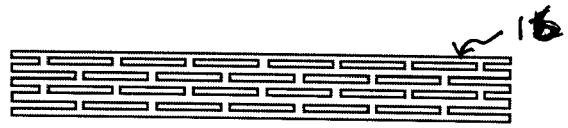
Figure 5:
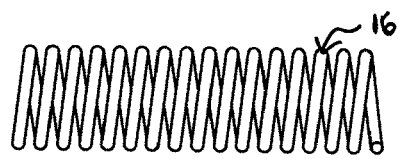
Figure 6:
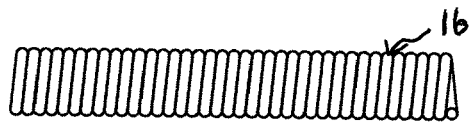
Figure 7:
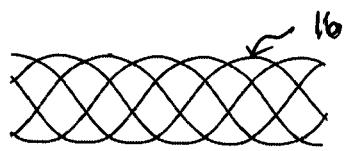
Figure 8:
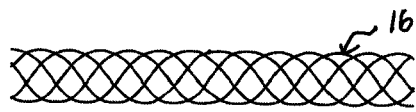
Figure 9:
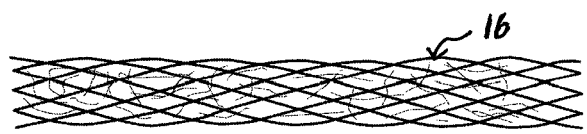
Figure 13:
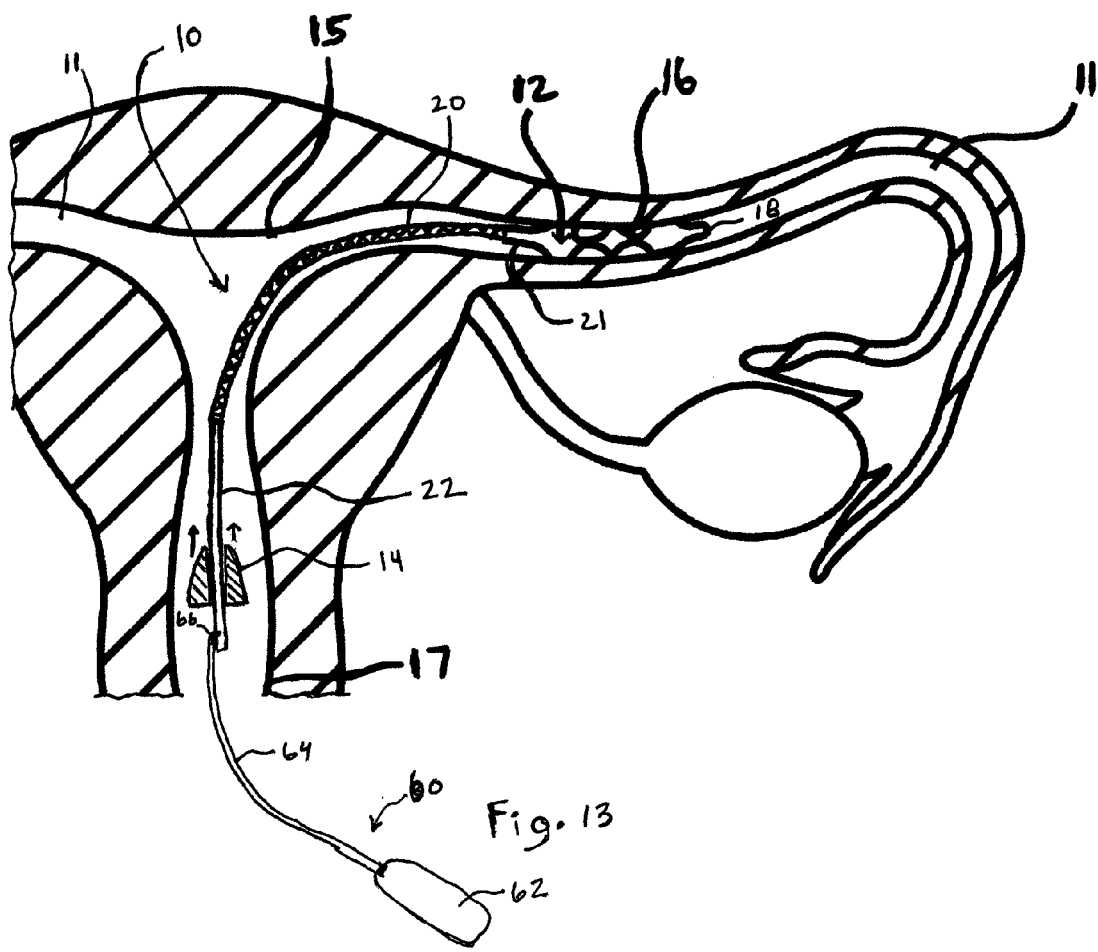
FIG. 13 schematically shows the delivery and insertion of primary and secondary occluding devices in accordance with embodiments of the present invention.

As shown in the embodiments of FIG. 13, the second occluding device 14 can be brought into operative communication with the first occluding device 14 such that both devices are capable of selective insertion and positioning within the body lumen, e.g., the female fallopian tubes 11 or the vas deferens 19 of a male patient (FIG. 2).

Such a configuration promotes and effects improved contraception. For example, as described further herein, the occluding device 12 can be first inserted into the body lumen, followed by insertion of the occluding device 14 to provide for secondary and primary occlusion, respectively. While the devices 12, 14 are described herein as having exemplary configurations, the dimensions, materials, shapes, and sizes can vary greatly to promote the desired occlusion of the body lumen. Further, the procedures and steps described herein can be employed bilaterally, e.g., to both fallopian tubes 11.

Figure 14:
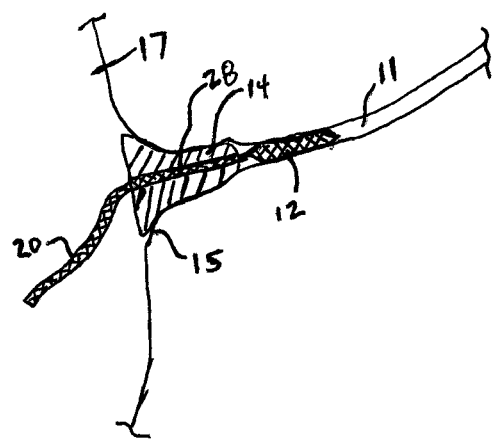
FIG. 14 schematically shows the positioning of primary and secondary occluding devices, having an extending tail member, within a body lumen in accordance with embodiments of the present invention.
Figure 15:
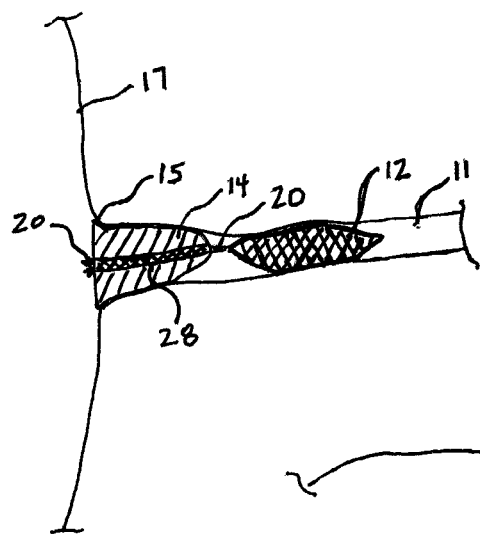
FIG. 15 schematically shows the positioning of primary and secondary occluding devices, having a trimmed tail member, within a body lumen in accordance with embodiments of the present invention.

Referring generally to FIGS. 13-15, the first occluding device 12 can include a tail member or portion 20 extending from a portion of the first occluding device 12. The tail portion 20 can be a polymer material, such as a mesh strip, of a predetermined length. In one embodiment, the tail portion 20 can extend such that at least a length will trail out the ostium 15 and into the uterus 17. Further, the tail portion 20 can include a rod member 22 in certain embodiments. The rod member 22 can extend from the mesh tail portion 20 and can be shaped, sized and configured to receive or travel along at least a portion of the second occluding device 14. In various embodiments, the tail portion 20 can be constructed of known compatible materials, such as polymer mesh, non-mesh materials, solid members, and the like. The tail portion 20 and/or rod member 22 can be generally flexible, semi-rigid, or rigid, and can extend from any portion of the device 12.

Figure 10:
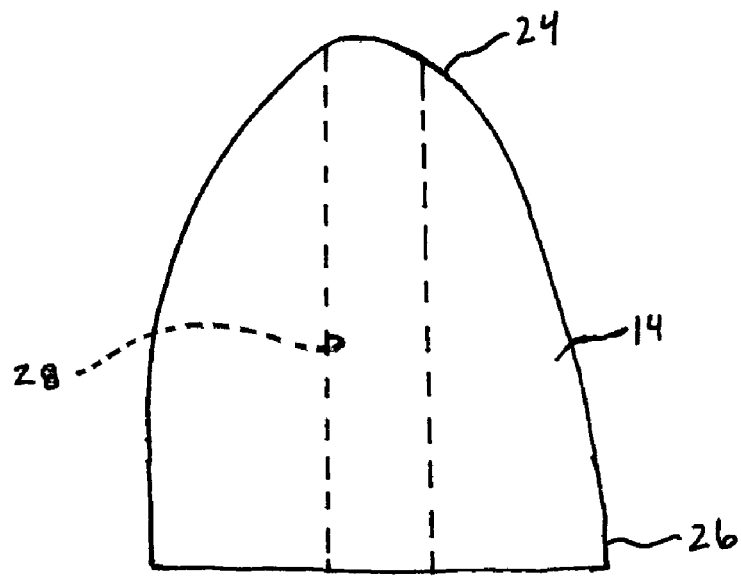
FIGS. 10-11 show exemplary occluding devices in accordance with embodiments of the present invention.
Figure 11:
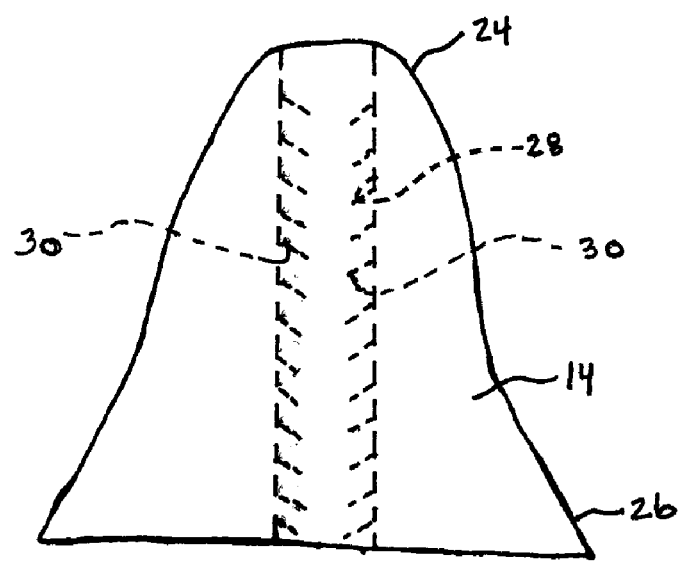

The second occluding device 14 can include a first end 24, a second end 26 and an inner lumen 28 extending from the first end 24 to the second end 26, as shown in FIGS. 10-11. In certain embodiments, the device 14 can be tapered such that the second end 26 is larger in cross-section than the first end 26. In other embodiments, the device 14 can take on a myriad of acceptable shapes and designs, including a bell-shape, tubular, flanged, lattice construction and like shapes or structures. Further, the occluding device 14 can be constructed of various polymer or other known compatible materials, including solid, mesh, non-mesh and like constructs.

In certain embodiments, the inner lumen 28 can include a plurality of extending protrusions or members 30 (e.g., angled teeth members, fibers, etc.) adapted to grab and retain sections of the tail portion 20 of the occluding device 12 during insertion and positioning of the devices. In other embodiments, the inner lumen 28 can include one or more textured portions adapted to facilitate gripping and retention of the tail portion 20. In addition, the outer surface of the device 14 can include one or more textured portions, protruding members, fibers, etc., to facilitate attachment of the device 14 against or within body tissue.

Figure 12:
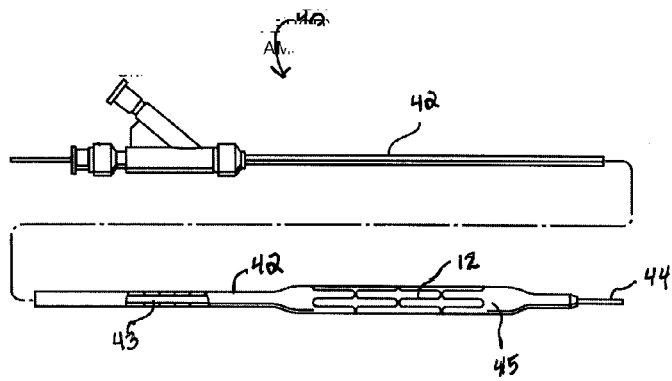
FIG. 12 shows an exemplary catheter delivery system for use in delivering an occluding device in accordance with embodiments of the present invention.

Referring generally to FIGS. 1 and 12, an embodiment of a catheter delivery system 40 is shown. The catheter system 40 can include an elongated shaft 42 having a lumen 43 which is in communication with a member 44 on a distal portion 45 of the catheter shaft 42. The occluding device (e.g., device 12) can be disposed at the distal shaft 42, within the lumen 43 of the shaft 42, or along the member 44 extending from the shaft 42. The occluding device 12 can be formed so that it has a collapsed configuration (e.g., with shape memory) with relatively small transverse dimensions. For example, the occluding device 12 may be deformed to facilitate mounting or disposal onto or within the shaft 42 and is expandable to an open expanded configuration within a body lumen when deployed from the catheter 40. Other known catheter delivery systems, and occluding systems and members, can be employed with the present invention, including those disclosed in U.S. Pat. No. 7,073,504, and U.S. Patent Publication Nos. 2005/0045183, 2005/0209633, 2007/0261699, 2008/0135054 and 2008/0308110, each of which is hereby incorporated by reference in its entirety.

Upon deployment to the body lumen (e.g., through the uterus, ostium and into the fallopian tube 11), the device 12 can be expanded to a larger dimension. The expansion of the diameter of occluding device 12 can be effected either by use of an expanding device, e.g., an inflatable balloon at the delivery catheter distal end that is disposed within the catheter lumen 44, or by self-expansion upon release from confinement within the delivery catheter. In an expanded configuration, the device 12, and tubular member 16 in particular, has an open, lattice-type structure facilitating epithelialization or tissue in-growth. Such tissue in-growth assists in securing the occluding device 12 to the tissue wall of the reproductive tract or body lumen. In one embodiment, the device 12 is expanded or self-expands to a diameter equal to or slightly larger than the inner diameter of the respective body lumen. For example, the expanded transverse dimension or diameter of the tubular member 16 can be approximately 0.1 mm to about 5 mm for disposition and retention within a female patient's fallopian tubes 11. The catheter 40 can be advanced under fluoroscopic or endoscopic visualization to a location within one of the female patient's fallopian tubes 11 until occluding device 12 is positioned within one of the female patient's fallopian tubes 11.

FIGS. 13-16 show insertion and deployment techniques for the second occluding device 14. In one embodiment, a delivery tool 60 can be used to insert, direct and position the occluding device 14 within the uterus and into the uterine ostium 15, or the body lumen 11. The delivery tool 60 can include a handle portion 62, a needle portion 64, with the needle portion 64 including a distal end portion 66. The needle portion 64 can be straight, curved, helical, or can take on any other shape or configuration adapted to facilitate insertion, maneuvering around anatomical structures, and deployment of the device 14 within the patient. In certain embodiments, the needle portion 64 is curved to better assist in pushing the occluding device 14 into the ostium 15 without visually observing the implant. Embodiments of the delivery tool 60 can take on various know forms, and/or employ the delivery techniques as disclosed in PCT International Application Publication Nos. WO2009/075800 and WO2009/017680, which are incorporated by reference herein in their entirety.

The device 14 is adapted to travel or slide along the tail 20 (and/or rod member 22) such that the tail 20 passes through the lumen 30 of the device 14. Upon traversal of the device 14 along the tail 20 via the tool 60, the device 14 can be inserted into and positioned within the uterine ostium 15 of the patient. Upon deployment, at least a portion of the tail 20 is generally extending from the second end 26 of the device 14. At this point, the tail 20 can be cut off or otherwise removed proximate the device 14. Alternatively, the tail 20, or a portion thereof, can remain extending into the uterus 17 of the patient to provide further occlusion (e.g., act as an intra-uterine device). A compatible adhesive, gel or like material can be applied to the juncture between the extending tail 20 and the second end 26 of the lumen 30 to seal openings or gaps.

Figure 16:
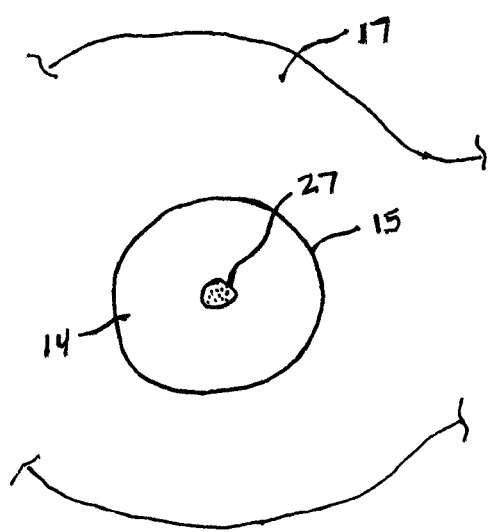
FIG. 16 schematically shows a plug inserted within a lumen of an occluding device in accordance with embodiments of the present invention.

For those embodiments where the tail 20 is removed or cut off at or proximate the occluding device 14, various structures or techniques can be implemented to seal off the lumen 30 at the second end 26 of the device 14. For example, a plug 27 can be inserted into the second end 26 of the lumen 30 to close off the opening, as shown in FIG. 16. The plug 27 can also serve to push any remaining portion of the tail 20 into the lumen 30 (e.g., bunching the remaining tail 20 within the lumen 30). In certain other embodiments, a compatible adhesive, gel or like material can be inserted into the second end 26 of the lumen 30. Sealing or closing off of the lumen 30 can provide additional occlusion benefits.

The disclosed embodiments of the present invention utilize both occluding devices 12, 14 to provide a primary and secondary occlusion system and method. Namely, a relatively quick initial primary occlusion occurs when the occluding device 14 is inserted into the ostium 15 and a secondary long-term occlusion occurs with the insertion of the occluding device 12 within the fallopian tubes 11 (e.g., tissue ingrowth within the device 12). As such, the device 14 serves as a primary occluder and the device 12 serves as a secondary occluder. A third mechanism for occlusion and contraception is provided for those embodiments where the tail 20 is left to extend into the uterus 17 as an intra-uterine device.

All patents and publications referenced herein are hereby incorporated by reference in their entireties.

It will be understood that certain of the described structures, functions and operations of the above-described preferred embodiments are not necessary to practice the present invention and are included in the description simply for completeness of an exemplary embodiment or embodiments. It will also be understood that there may be other known structures, functions and operations ancillary to the typical surgical procedures that are not disclosed, but that can be implemented to practice the present invention. It is, therefore, to be understood that within the scope of the appended claims, the invention may be practiced other than as specifically described without actually departing from the spirit and scope of the present invention.

What is claimed is:

1. A method of occluding a patient's body lumen, comprising:
    advancing a delivery catheter tool at least partially receiving a first occluding device therein to a location within a fallopian tube of a patient, wherein the first occluding device includes a tail member, and a first transverse configuration within the delivery catheter tool;
    deploying the first occluding device from the delivery catheter tool and within the fallopian tube, wherein the deployed first occluding device comprises a radially expanded configuration with a second transverse dimension larger than the first transverse dimension;
    operatively coupling at least a portion of the tail member of the first occluding device within a lumen extending through a second occluding device; and
    slidably delivering the second occluding device distally along the extending tail member to a uterine ostium of the patient proximate the first occluding device after delivering the first occluding device from the delivery catheter tool within the fallopian tube.

2. The method of claim 1, wherein slidably delivering the second occluding device is performed with a delivery tool having a curved needle portion.

3. The method of claim 1, further including removing at least a portion of the tail member extending from the lumen of the second occluding device.

4. The method of claim 3, further including plugging an end portion of the lumen of the second occluding device.

5. The method of claim 1, wherein the tail member comprises a polymer.

6. The method of claim 1, wherein the first occlusion device self-expands when deploying from the delivery catheter tool within the fallopian tube.

7. The method of claim 1, wherein the first occlusion device comprises fibers to support tissue ingrowth.

8. The method of claim 1, wherein the first occluding device includes a mesh portion.

* * * * *